(12) United States Patent
Du

(10) Patent No.: US 12,083,203 B2
(45) Date of Patent: Sep. 10, 2024

(54) COSMETIC COMPOSITION

(71) Applicant: Merry Plus Corporation, Tokyo (JP)

(72) Inventor: Yao Du, Tokyo (JP)

(73) Assignee: Merry Plus Corporation, Tokyo (JP)

( * ) Notice: Subject to any disclaimer, the term of this patent is extended or adjusted under 35 U.S.C. 154(b) by 0 days.

(21) Appl. No.: 18/147,740

(22) Filed: Dec. 29, 2022

(65) Prior Publication Data

US 2023/0149276 A1    May 18, 2023

Related U.S. Application Data

(63) Continuation of application No. PCT/JP2021/024796, filed on Jun. 30, 2021.

(30) Foreign Application Priority Data

| Jul. 1, 2020 | (JP) | 2020-113773 |
| Feb. 24, 2021 | (JP) | 2021-027488 |

(51) Int. Cl.

| A61K 8/02 | (2006.01) |
| A61K 8/06 | (2006.01) |
| A61K 8/31 | (2006.01) |
| A61K 8/39 | (2006.01) |
| A61K 8/92 | (2006.01) |
| A61Q 1/14 | (2006.01) |

(52) U.S. Cl.
CPC .............. *A61K 8/39* (2013.01); *A61K 8/068* (2013.01); *A61K 8/31* (2013.01); *A61Q 1/14* (2013.01); *A61K 2800/262* (2013.01)

(58) Field of Classification Search
None
See application file for complete search history.

(56) References Cited

U.S. PATENT DOCUMENTS

| 2007/0248631 A1 | 10/2007 | Takase |
| 2013/0059764 A1 | 3/2013 | Tashiro |
| 2014/0134125 A1 | 5/2014 | Dahl |
| 2014/0227217 A1 | 8/2014 | Matsuzawa |
| 2017/0156998 A1 * | 6/2017 | Koide ............... A61K 8/068 |
| 2020/0405591 A1 | 12/2020 | Mizuno |
| 2022/0023163 A1 | 1/2022 | Niimi |
| 2022/0047477 A1 | 2/2022 | Maruyama |

FOREIGN PATENT DOCUMENTS

| DE | 102011078382 A1 | 1/2013 |
| EP | 2762129 A1 | 8/2014 |
| JP | H9-110635 A | 4/1997 |
| JP | 3667046 B | 7/2005 |
| JP | 2006-45197 A1 | 2/2006 |
| JP | 2011-241156 A | 12/2011 |
| JP | 2014-122197 A | 7/2014 |
| JP | 2016-88883 A | 5/2016 |
| JP | 2016-108262 A | 6/2016 |
| JP | 2018-16613 A1 | 2/2018 |
| JP | 2019-218300 A | 12/2019 |
| JP | 2020-83819 A | 6/2020 |
| JP | 2020-090469 A | 6/2020 |
| WO | 2019168193 A1 | 9/2019 |
| WO | 2019244908 A1 | 12/2019 |
| WO | 2020/122087 A1 | 6/2020 |

OTHER PUBLICATIONS

International Search Report from International Application No. PCT/JP2021/024796 mailed Aug. 31, 2021.

* cited by examiner

*Primary Examiner* — Brian Gulledge
(74) *Attorney, Agent, or Firm* — Shih IP Law Group, PLLC.

(57) ABSTRACT

One object is to provide a cosmetic composition having high transparency, high stability, good feeling of use and high cleansing power. There is provided a cosmetic composition in a form of an oil-in-water type microemulsion, comprising: (a) at least one type of an oil; (b) a polyglycerol fatty acid monoester having an HLB value of 11 to 18; (c) a polyglycerol fatty acid diester or a polyglycerol fatty acid triester having an HLB value of 10 to 13 and having an alkyl chain or an alkenyl chain of ten to fourteen carbon atoms; (d) an anionic surfactant; and (e) water, wherein a mass ratio of the (c) polyglycerol fatty acid diester or polyglycerol fatty acid triester to the (b) polyglycerol fatty acid monoester is 0.01 to 1.65, and a ratio of a total mass of the (b) the polyglycerol fatty acid monoester and the (c) polyglycerol fatty acid diester or polyglycerol fatty acid triester to a mass of the (a) oil is 1 to 550.

13 Claims, No Drawings

COSMETIC COMPOSITION

TECHNICAL FIELD

The present disclosure relates to a cosmetic composition in the form of an oil-in-water type microemulsion.

BACKGROUND

Compositions in the form of emulsions have been widely used in the field of cosmetics. Especially, fine emulsions such as microemulsions have been highly demanded, because of the transparency or the translucency of the appearance.

Cleansing cosmetics are, on the other hand, generally rinsed off with water after being applied on the skin or are wiped off with a tissue or the like. Various forms of cleansing cosmetics are commercially available. A water-based form and an oil-in-water type emulsion provide good feeling of use but have a disadvantage of low cleansing effects. An oil form and a water-in-oil type emulsion provide high cleansing effects but still have a room for improvement in the feeling of use, because of the stickiness and the difficulty in being rinsed off with water. The oil form and the water-in-oil type have low cleansing power and poor feeling of use on the wet skin and accordingly need further improvement.

A microemulsion is effective for improvement of the various problems described above. The microemulsion is a system that makes a larger amount of an oil (or water) soluble than a general micelle solution (or a reverse micelle oil solution) and is an isotropic solution having the transparent to blue appearance. Like a general macroemulsion, the microemulsion includes an oil-in-water type (O/W, Patent Literatures 1 to 3) and a water-in oil type (W/O, Patent Literature 4).

The water-in-oil type microemulsion as a cleansing cosmetic described in Patent Literature 4 allows for addition of a larger amount of water than the general reverse micelle solution and has such an advantage that the cleansing power is not significantly reduced even on the wet skin. The water-in-oil-type microemulsion having the oil outer phase, however, has a lower affinity to water-based makeup stains compared with the oil-in-water type microemulsion and has low cleansing power against such stains. Another disadvantage of the water-in-oil type microemulsion has a higher viscosity than the viscosity of the water-based form and the resulting inability to use with cotton. The oil-in-water type microemulsion, on the other hand, needs to minimize the interfacial tension to maintain the transparency and improves the cleansing power by the synergistic effect of the low interfacial tension and the oil to be added.

Polyglycerol fatty acid esters having the high safety have conventionally been used as a non-ionic surfactant to form a microemulsion. The polyglycerol fatty acid esters, however, have low emulsifying capacity and require a large amount to be added for preparation of the microemulsion. The polyglycerol fatty acid esters also have problems of insufficient stability and the possibility of creaming or the like.

There are disclosures that the stability of the microemulsion is enhanced by inclusion of a 2-hydroxy fatty acid of ten to twenty two carbon atoms (Patent Literature 1) or inclusion of betaine acid (Patent Literature 2) as an auxiliary emulsifying agent, in addition to the polyglycerol fatty acid ester. Patent Literature 3 discloses a cosmetic composition including (a) at least one type of an oil; (b) at least one type of a first (poly)glycerol fatty acid ester surfactant having a (poly)glyceryl moiety derived from one to ten glycerol molecules and having one or a plurality of C12-20 alkyl chains or alkenyl chains; (c) at least one type of a second (poly)glycerol fatty acid ester surfactant having a (poly)glyceryl moiety derived from one to ten glycerol molecules and having one or a plurality of C6-10 alkyl chains or alkenyl chains; (d) at least one type of a polyol; and (e) water. The disclosure shows that the combination of the polyol with the first and the second (poly)glycerol fatty acid esters provides a disperse phase of the small diameter.

Patent Literature 5 discloses an oil-in-water type cleansing cosmetic that is not in the form of a microemulsion but that includes two types of polyglycerol fatty acid esters having an HLB value of 10 to 17 and at least one type of a non-ionic surfactant.

CITATION LIST

Patent Literature

Patent Literature 1: JP H09-110635A
Patent Literature 2: JP No. 3667046B
Patent Literature 3: JP 2014-122197A
Patent Literature 4: JP 2006-45197A
Patent Literature 5: JP 2018-16613A

SUMMARY

Technical Problem

In Patent Literature 1, however, the hydroxy fatty acid having ten to 22 carbon atoms is essential for the stable microemulsion. The polyglycerol fatty acid ester used is an ester of a C12 to C18 fatty acid having a high molecular weight and polyglycerol and is also limited to a monoester. In application as a cleansing cosmetic, Patent Literature 1 provides only insufficient cleansing power. Patent Literature 2 refers to only applications for leave-on prescription such as moisturizing lotions and milky lotions. For example, in application as a cleansing cosmetic, Patent Literature 2 using an ester of a C12 to C18 fatty acid having a high molecular weight and polyglycerol provides only insufficient cleansing power. In Patent Literature 3, a polyol is essential for formation of a nano-emulsion or a microemulsion. For example, in application as a cleansing product, Patent Literature 3 provides poor feeling of freshness that is one of the feelings of use.

The oil-in-water type cleansing cosmetic of Patent Literature 5 has good balance between water and oil and tries to well control the cleansing power and the stickiness after rinse-off. Such a milky lotion-type cleansing cosmetic, however, requires to add an (acrylates/alkyl acrylate) crosspolymer and a higher alcohol for the enhanced emulsion stability and to provide an appropriate viscosity by using a water-soluble thickening agent or the like. This emulsion type cleansing cosmetic may reduce the stickiness after rinse-off with water but has poor feeling of freshness due to the stickiness caused by the water-soluble thickening agent such as the (acrylates/alkyl acrylate) crosspolymer. Furthermore, the viscosity is provided by using the thickening agent. This cleansing cosmetic is accordingly not suitable for wiping use with a sheet base material such as cotton or for use in a pump foamer. Moreover, this cleansing cosmetic is not in the form of a microemulsion and accordingly has the lack of transparency and the lack of the visual sensation of coolness and the sense of luxury characteristic of water-based cleaning cosmetics. These prior arts have not yet succeeded in providing a cleansing cosmetic of good water-oil balance that has the feeling of freshness during an application on the skin, that does not need to be rinsed off, that is suitable for wiping use with cotton and for use in a pump foamer.

An object of the present disclosure is to provide a cosmetic composition having high transparency, high stability and good feeling of use. A further object of the present disclosure is to provide a cosmetic composition, in application as a cleansing cosmetic, that has affinity to both water-based and oil-based makeup stains to provide the high cleansing power and that provides the feeling of freshness even in the case of wiping use with a sheet base material (even in the case where the cosmetic composition is not rinsed off with water).

Solution to Problem

According to one aspect of the invention, there is provided a cosmetic composition in a form of an oil-in-water type microemulsion, comprising: (a) at least one type of an oil; (b) at least one type of a polyglycerol fatty acid monoester having an HLB value of 11 to 18; (c) at least one type of a polyglycerol fatty acid diester or a polyglycerol fatty acid triester having an HLB value of 10 to 13 and having an alkyl chain or an alkenyl chain of ten to fourteen carbon atoms; (d) at least one type of an anionic surfactant; and (e) water. A mass ratio of the (c) polyglycerol fatty acid diester or polyglycerol fatty acid triester to the (b) polyglycerol fatty acid monoester is 0.01 to 1.65. A ratio of a total mass of the (b) the polyglycerol fatty acid monoester and the (c) polyglycerol fatty acid diester or polyglycerol fatty acid triester to a mass of the (a) oil is 1 to 550.

In the cosmetic composition of the above aspect, it is preferable that the cosmetic composition having a viscosity of 0.1 to 100 mPa·s at 30° C.

In the cosmetic composition of the above aspect, it is preferable that the cosmetic composition does not substantially include a polyol.

In the cosmetic composition of the above aspect, it is preferable that the cosmetic composition does not substantially include (acrylates/C10-30 alkyl acrylate) crosspolymer.

In the cosmetic composition of the above aspect, it is preferable that the (b) polyglycerol fatty acid monoester has a polyglyceryl moiety derived from two to ten glycerol molecules and an alkyl chain or an alkenyl chain of six to twelve carbon atoms, and the (c) polyglycerol fatty acid diester or polyglycerol fatty acid triester is a polyglycerol fatty acid diester having a polyglyceryl moiety derived from two to ten glycerol molecules.

In the cosmetic composition of the above aspect, it is preferable that the (b) polyglycerol fatty acid monoester has a polyglyceryl moiety derived from two to ten glycerol molecules and an alkyl chain or an alkenyl chain having six to twelve carbon atoms, and the (c) polyglycerol fatty acid diester or polyglycerol fatty acid triester is a polyglycerol fatty acid triester having a polyglyceryl moiety derived from two to ten glycerol molecules.

In the cosmetic composition of the above aspect, it is preferable that a mass ratio of the (c) polyglycerol fatty acid diester or polyglycerol fatty acid triester to the (b) polyglycerol fatty acid monoester is 0.6 to 1.1.

In the cosmetic composition of the above aspect, it is preferable that a mass average HLB value of a mixture of the (b) polyglycerol fatty acid monoester and the (c) polyglycerol fatty acid diester or polyglycerol fatty acid triester is 10.5 to 14.5.

In the cosmetic composition of the above aspect, it is preferable that the (b) polyglycerol fatty acid monoester is polyglyceryl-6 caprylate, and the (c) polyglycerol fatty acid diester is polyglyceryl-6 dicaprate.

In the cosmetic composition of the above aspect, it is preferable that the (b) polyglycerol fatty acid monoester is polyglyceryl-6 caprylate, and the (c) polyglycerol fatty acid triester is polyglyceryl-10 trilaurate.

In the cosmetic composition of the above aspect, it is preferable that a ratio of a total mass of the (b) polyglycerol fatty acid monoester and the (c) polyglycerol fatty acid diester or polyglycerol fatty acid triester to a mass of the (a) oil is 1.66 to 30.

In the cosmetic composition of the above aspect, it is preferable that the (d) anionic surfactant is at least one type of a surfactant selected from amino acid surfactants and isethionic acid surfactants.

In the cosmetic composition of the above aspect, it is preferable that the (a) oil is a hydrocarbon oil, an ether oil, or an ester oil.

In the cosmetic composition of the above aspect, it is preferable that the cosmetic composition being applied to a wiping-type cleansing cosmetic or a leave-on cosmetic.

The present disclosure provides the cosmetic composition that has high transparency and high stability and provides good feeling of use. Furthermore, in application as a cleansing cosmetic, the cosmetic composition has affinity to both water-based and oil-based makeup stains to provide the high cleansing power. Furthermore, the cosmetic composition of the present disclosure has a low viscosity and thus allows for wiping use with cotton or the like or for use in a pump foamer, when being applied as a cleansing cosmetic. Moreover, the present disclosure provides the cosmetic composition that has low stickiness and good feeling of freshness even in the state that the composition is not rinsed off with water, and is thereby suitable for cleansing cosmetics of the wiping use-type with cotton or the like and for leave-on products (skincare products, makeup products and the like intended to be left on the skin, for example, skin lotions, milky lotions, creams, and cosmetic face masks).

DESCRIPTION OF EMBODIMENTS

The inventor of the present application has found that a composition in the form of an oil-in-water type microemulsion which has high transparency and high stability and, in application as a cleaning cosmetic, has high cleansing power against both oil-based and water-based makeup stains is obtained by mixing polyglycerol fatty acid esters with keeping a mass ratio of a polyglycerol fatty acid monoester to a polyglycerol fatty acid diester or to a polyglycerol fatty acid triester in a predetermined range and keeping a ratio of a total mass of the polyglycerol fatty acid monoester and the polyglycerol fatty acid diester or the polyglycerol fatty acid triester to a mass of an oil.

A cosmetic composition according to the present disclosure comprises (a) at least one type of an oil; (b) at least one type of a polyglycerol fatty acid monoester; (c) at least one type of a polyglycerol fatty acid diester or a polyglycerol fatty acid triester; (d) at least one type of an anionic surfactant; and (e) water, wherein a mass ratio of the polyglycerol fatty acid diester to the polyglycerol fatty acid monoester is 0.01 to 1.65 and a ratio of a total mass of the polyglycerol fatty acid monoester and the polyglycerol fatty acid diester or the polyglycerol fatty acid triester to a mass of the oil is 1 to 550.

The cosmetic composition of the present disclosure is in the form of microemulsion. The "microemulsion" is defined in two senses, i.e., in a broad sense and in a narrow sense. The "microemulsion in the narrow sense" indicates thermodynamically stable isotropic single liquid phase having a three component system consisting of three components, i.e., an oil-based component, a water-based component and a surfactant. The "microemulsion in the broad sense", on the other hand, additionally includes emulsions having the transparent or translucent appearance due to the smaller particle size in a thermodynamically unstable typical emulsion system (refer to Satoshi TOMOMASA et al., Oil Chemistry, Vol. 37, No. 11 (1988), pp 48-53). The term "microemulsion" used in the description hereof is the "microemulsion in the narrow sense" and more specifically indicates the thermodynamically stable isotropic single liquid phase. The "microemulsion" is an optically transparent or translucent microdroplet dispersion system that is formed from water, oil, and a surfactant and that has the particle diameter of micelle of about several nm to several hundred nm.

The viscosity of the cosmetic composition of the present disclosure measured at 30° C. by a B-type (Brookfield) viscometer is preferably 0.1 to 100 mPa·s and is more preferably 0.1 to 50 mPa·s. Such a low viscosity allows for the use as a wiping type with a sheet base material or for the use in a pump foamer. The use as the wiping type with the sheet base material may be, for example, a method of wiping the skin with a cotton sheet or the like impregnated with the cosmetic composition to remove a stain such as a makeup stain or a method of applying the cosmetic composition on a site of the skin with a stain such as a makeup stain to spread over the site and then wiping off the cosmetic composition to remove the stain with a cotton sheet or the like. The pump foamer herein includes a squeeze foamer that pushes out the content in the form of foams when a vessel is squeezed with a hand, as well as a pump-up foamer that pushes out the content in the form of foams by a pumping action.

The cosmetic composition of the present disclosure has non-substantial inclusion of a polyol. The expression of "non-substantial inclusion" means a level that does not affect the feeling of freshness and is preferably a level of lower than 1.0% by mass. Non-substantial inclusion of the polyol assures the feeling of freshness without stickiness especially when the cosmetic composition is used for a leave-on cosmetic or for a cleansing cosmetic of wiping use-type with cotton or the like, i.e., for a cleansing cosmetic with the composition left on the skin. The polyol serves to change the clouding point of the components (b) and (c) polyglycerol fatty acid esters and thereby significantly affects formation of the microemulsion. The configuration of the present disclosure is characterized by formation of a stable microemulsion without a polyol.

For reasons of the viscosity, the feeling of use and the like, it is preferable that the cosmetic composition of the present disclosure does not include (acrylates/C10-30 alkyl acrylate) crosspolymer. The (acrylates/C10-30 alkyl acrylate) crosspolymer is a water-soluble thickening agent and is obtained by crosslinking a copolymer of one or more types of monomers, such as acrylic acid, methacrylic acid or simple esters thereof, and an alkyl acrylate (having the number of carbons of 10 to 30) with an aryl ether of sucrose or with an aryl ether of pentaerythritol. It is also preferable that the cosmetic composition of the present disclosure does not contain a water-soluble or hydrophilic thickening agent such as carbomer or xanthan gum.

Examples of the (a) oil used according to the present disclosure include vegetable oils, such as olive oil, camelia oil, safflower oil, jojoba oil, sunflower oil, almond oil, macadamia nut oil, linseed oil, corn oil, olive oil, avocado oil, sesame oil, soybean oil and peanut oil; animal oils, such as egg yolk oil, beef tallow, lard, mutton tallow, yellow bees wax, turtle oil, mink oil, shark liver oil, spermaceti and lanolin; hydrocarbon oils, such as hexane, undecane, dodecane, isohexadecane, isododecane, squalane, squalene, liquid paraffin, petrolatum, polydecene, hydrogenated polyisobutene, naphthalene, isoeicosane, microcrystalline wax and decene/butene copolymer; ether oils, such as dicaprylyl ether; ester oils, such as dicaprylyl carbonate, isopropyl lauroyl sarcosinate, isononyl isononanoate, cetyl octanoate, isodecyl neopentanoate, myristyl propionate, 2-ethylhexyl caprylate/caprate, isopropyl myristate, isostearyl palmitate, ethyl laurate, diethyl sebacate, diisopropyl adipate, and glyceryl tricaprate/tricaprylate; silicone oils, such as dimethylpolysiloxane and methyl phenyl polysiloxane; higher alcohols, such as lauryl alcohol, stearyl alcohol, and cetanol; and fatty acids, such as lauric acid and stearic acid. The (a) oil may be one type of the oil or two or more types of the oils selected among them. When the cosmetic composition of the present disclosure is used as a cleansing cosmetic, in terms of the enhanced cleansing power, the hydrocarbon oils and the ether oils are especially preferable. When the cosmetic composition of the present disclosure is used as a skin lotion or the like, the ester oils are preferable. The ratio of the mass of the (a) oil to the total mass of the composition is preferably 0.02 to 30% by mass and is more preferably 0.2 to 15% by mass.

The (b) polyglycerol fatty acid monoester used according to the embodiment is an ester consisting of one fatty acid and polyglycerol and has an HLB value of 8 to 18 or preferably 11 to 18. The polyglycerol fatty acid monoester preferably has a polyglyceryl moiety derived from two to ten glycerol molecules or preferably four to ten glycerol molecules.

In the description of this embodiment, HLB (Hydrophilic-Lipophilic Balance) is an index indicating the degrees of affinity of the surfactant to water and oil and is calculated by the Griffin's equation (J. Soc. Cosmet. Chem., 1,311(1949); 5,249(1953)). The HLB value of a surfactant mixture comprised of two or more different types of non-ionic surfactants (hereinafter referred to as mixture HLB) is a weighted average of the HLB values of the respective non-ionic surfactants on the basis of their mixing ratio and is obtained by an equation given below:

$$\text{Mixture HLB Value} = \Sigma(\text{HLB}x \times Wx)/\Sigma Wx$$

(where HLBx represents an HLB value of a surfactant X, and Wx represents a mass (g) of the surfactant X having the value of HLBx).

The (b) polyglycerol fatty acid monoester used according to the present disclosure preferably has a lower molecular weight. The lower molecular weight provides the higher cleansing power in application as a cleansing cosmetic. The (b) polyglycerol fatty acid monoester is an ester of a saturated acid or an unsaturated acid preferably having six to twelve carbon atoms or more preferably having eight to ten carbon atoms and preferably has an alkyl chain or an alkenyl chain preferably having six to twelve carbon atoms or more preferably having eight to ten carbon atoms. A preferable example is a monoester of capric acid or caprylic acid and polyglycerol.

Concretely, the (b) polyglycerol fatty acid monoester may be one type or two or more types of polyglycerol fatty acid monoesters selected from the group consisting of polyglyceryl-2 caprate, polyglyceryl-2 caprylate, polyglyceryl-3 caprate, polyglyceryl-3 caprylate, polyglyceryl-4 caprate, polyglyceryl-4 caprylate, polyglyceryl-5 caprate, polyglyceryl-5 caprylate, polyglyceryl-6 caprate, polyglyceryl-6 caprylate, polyglyceryl-10 caprate, polyglyceryl-10 caprylate, polyglyceryl-2 laurate, polyglyceryl-3 laurate, polyglyceryl-4 laurate, polyglyceryl-5 laurate, polyglyceryl-6 laurate, and polyglyceryl-10 laurate.

The (c) polyglycerol fatty acid diester used according to the embodiment is an ester consisting of two fatty acids and polyglycerol and has an HLB value of 7 to 13 or preferably 10 to 13. The polyglycerol fatty acid diester preferably has a polyglyceryl moiety derived from two to ten glycerol molecules or preferably five to ten glycerol molecules.

The (c) polyglycerol fatty acid diester used according to the embodiment is a diester of a saturated or unsaturated acid preferably having six to eighteen carbon atoms or more preferably having ten to eighteen carbon atoms and preferably has an alkyl chain or an alkenyl chain preferably having six to eighteen carbon atoms, more preferably having ten to eighteen carbon atoms, and furthermore preferably having ten to fourteen carbon atoms. A preferable example is a diester of capric acid and polyglycerol.

Concretely, the polyglycerol fatty acid diester may be one type or two or more types of polyglycerol fatty acid diesters selected from the group consisting of polyglyceryl-5 dioleate, polyglyceryl-6 dicaprate, polyglyceryl-10 dimyristate, polyglyceryl-10 dioleate, polyglyceryl-10 distearate, and polyglyceryl-1-diisostearate.

The (c) polyglycerol fatty acid triester used according to the embodiment is an ester consisting of three fatty acids and polyglycerol and has an HLB value of 7 to 13 or preferably 10 to 13. The polyglycerol fatty acid triester preferably has a polyglyceryl moiety derived from two to ten glycerol molecules or preferably five to ten glycerol molecules. The (c) polyglycerol fatty acid triester used according to the embodiment is a triester of a saturated or unsaturated acid preferably having six to eighteen carbon atoms or more preferably having ten to fourteen carbon atoms and preferably has an alkyl chain or an alkenyl chain preferably having six to eighteen carbon atoms, more preferably having ten to fourteen carbon atoms. Concretely, the (c) polyglycerol fatty acid triester may be one type or two or more types of polyglycerol fatty acid triesters selected from the group consisting of polyglyceryl-5 trimyristate, polyglyceryl-5 trioleate, polyglyceryl-6 trilaurate, polyglyceryl-10 trilaurate, polyglyceryl-10 trioleate, and polyglyceryl-10 tristearate.

Each of the (b) polyglycerol fatty acid monoester and the (c) polyglycerol fatty acid diester or polyglycerol fatty acid triester serves as a non-ionic surfactant. The ratio of the total mass of the (b) polyglycerol fatty acid monoester and the (c) polyglycerol fatty acid diester or polyglycerol fatty acid triester to the total mass of the composition is preferably 0.1 to 60% by mass or preferably 0.5 to 30% by mass.

The mass ratio of the (c) polyglycerol fatty acid diester or polyglycerol fatty acid triester (in the case of two or more types, the total mass thereof) to the (b) polyglycerol fatty acid monoester (in the case of two or more types, the total mass thereof) is preferably 0.01 to 1.65, is more preferably 0.4 to 1.3, and is furthermore preferably 0.6 to 1.1. The HLB value of a mixture of the (b) polyglycerol fatty acid monoester and the (c) polyglycerol fatty acid diester or polyglycerol fatty acid triester is preferably 10.5 to 14.5 and is more preferably 11 to 13 on mass average. The HLB value exceeding this range causes insufficient transparency and lowers the stability of the microemulsion.

The polyglycerol fatty acid dieter and the polyglycerol fatty acid monoester having a relatively low molecular weight have high cleansing power and are preferable for the cleansing cosmetics. For example, polyglyceryl-6 dicaprate used in Examples described later has the higher cleansing power than those of most monoesters, and a monoester, polyglyceryl-6 caprylate, has a low molecular weight and accordingly has the higher cleansing power than those of monoesters having high molecular weights.

The ratio of the total mass of the (b) polyglycerol fatty acid monoester and the (c) polyglycerol fatty acid diester (in the case of two or more types of (b) or (c), the total mass thereof) to the mass of the (a) oil (in the case of two or more types, the total mass thereof) is preferably 1 to 550, is more preferably 1.5 to 50 and is furthermore preferably 1.66 to 30. The ratio below this range lowers the stability of the microemulsion.

Available examples of the (d) anionic surfactant according to the present disclosure include amino acid surfactants, isethionic acid surfactants, carboxylates, sulfonates, sulfates, higher fatty acid salts, alkyl ether sulfates, taurine salts, sarcosine salts, citrates, galacturonic acid salts, and sulfosuccinates. Especially preferable are amino acid surfactants, isethionic acid surfactants, and taurine surfactants, in terms of the gentleness on the skin. The amino acid surfactant is preferably selected from N-acylated amino acid salts, for example, alkali metal salts, alkaline earth metal salts, ammonium salts, alkanol amine slats, and basic amino acid salts of N-acylated amino acids. The isethionic acid surfactant is preferably selected from acylated isethionic acid salts, for example, alkali metal salts, alkaline earth metal salts, ammonium salts, alkanol amine slats, and basic amino acid salts of acylated isethionic acid. The taurine surfactant is preferably selected from acylated taurine salts, for example, alkali metal salts, alkaline earth metal salts, ammonium salts, alkanol amine slats, and basic amino acid salts of acylated taurine. Concretely, the (d) anionic surfactant is preferably one type or two or more types of anionic surfactants selected from the group consisting of sodium cocoyl glycinate, potassium cocoyl glycinate, sodium lauroyl glycinate, sodium lauryl diaminoethyl glycinate, sodium cocoyl aspartate, sodium cocoyl glutamate, disodium cocoyl glutamate, triethanolamine lauroyl glutamate, sodium cocoyl isethionate, ammonium cocoyl isethionate, sodium lauroyl isethionate, sodium lauroyl methyl isethionate, sodium cocoyl taurine, sodium cocoyl methyl taurine, sodium lauroyl taurine, and sodium lauroyl methyl taurine.

The ratio of the total mass of the anionic surfactant to the total mass of the composition is preferably 0.01 to 5% by mass and is more preferably 0.04 to 2% by mass.

The anionic surfactant contributes to the stability of the microemulsion. Addition of the anionic surfactant reduces the required amount of the non-ionic surfactant. This reduces the total amount of the surfactants to be added and serves to enhance the gentleness on the skin. The anionic surfactant is accordingly required in applications other than the cleansing cosmetics. Addition of only a small amount of the anionic surfactant causes little load on the skin.

The cosmetic composition of the present disclosure may include additives other than those described above: for example, an amphoteric surfactant such as betaine, a non-ionic surfactant and an ionic surfactant other than those described above, a preservative such as paraben or phenoxy ethanol, a sequestering agent, such as EDTA or etidronic acid, a moisturizing agent such as polyol, a thickening agent, a UV screening agent, a vitamin or provitamin, an antioxidant, a chelating agent, a whitening agent, a blood circulation promoter, an anti-inflammatory agent, a germicidal agent, a texture improver, an opaquer, a coloring agent, a perfume material, and a vegetable extract.

The cosmetic composition of the present disclosure includes water. The amount of water is not specifically limited but may be, for example, 30 to 99% or preferably 60 to 97% relative to the total mass of the composition.

The cosmetic composition of the present disclosure is usable for skincare products such as skin lotions and milky lotions, and/or makeup products such as foundations and mascaras, and/or cleaning products such as makeup cleansing agents and shampoos, which are applicable to the skin, the hair, the mucous membrane, the nails, the eyelashes, the eyebrows, or the scalp. Especially preferable applications are face skin cleaning agents, hair cleaning agents, scalp cleaning agents, body cleaning agents, and bath cosmetics.

The following describes a method of preparing the cosmetic composition of the present disclosure.

A procedure heats water, an oil, and non-ionic surfactants including a polyglycerol fatty acid monoester and either a polyglycerol fatty acid diester or a polyglycerol fatty acid triester to 75 degrees Celsius, stirs the mixture to become homogeneous, adds an anionic surfactant, and cools down the mixture with stirring. When the mixture is cooled down to 45 degrees Celsius, the procedure adds and dissolves the other additives to and in the mixture and cools down the mixture to room temperature with stirring. The method of preparing the cosmetic composition of the present disclosure is, however, not limited to this procedure. For example, another employable procedure may dissolve all the components at 75° C. and cool down the mixture to room temperature.

The following discloses and describes the aspects of the present disclosure in more detail with reference to examples. These examples are, however, only illustrative and are not intended at all to limit the scope of the present disclosure.

EXAMPLES

Examples 1 to 19

Cleansing cosmetic compositions of examples were prepared by mixing respective components as shown in Table 1 and Table 2. More specifically, the compositions were obtained by heating components shown in a field 'A' of Table 1 to 75 degrees Celsius, stirring the mixture to become homogeneous, adding components shown in a field 'B', cooling down the mixture to 45 degrees Celsius with stirring, adding and dissolving components shown in a field 'C' to and in the mixture, and cooling down the mixture to room temperature with stirring. Numerical values in the tables show "% by mass" of the respective components relative to the total mass of the entire composition.

The HLB value of polyglyceryl-6 caprylate, the HLB value of polyglyceryl-6 dicaprate, and the HLB value of polyglyceryl-10 trilaurate used in the examples are respectively 14.6, 10.2, and 10.4. Concretely, 'SUNSOFT Q-8H-C' (manufactured by Taiyo Kagaku Co., Ltd.), 'SUNSOFT Q-102H-C' (manufactured by Taiyo Kagaku Co., Ltd.), and 'SUNSOFT Q-123Y-C' (manufactured by Taiyo Kagaku Co., Ltd.) were respectively used as polyglyceryl-6 caprylate, as polyglyceryl-6 dicaprate, and polyglyceryl-10 trilaurate.

In the tables, an average HLB value denotes a mass average value of the HLB value of the non-ionic surfactant including the polyglycerol fatty acid esters. In the tables, a mass ratio 1 denotes a mass ratio of the polyglycerol fatty acid diester to the polyglycerol fatty acid monoester or a mass ratio of the polyglycerol fatty acid triester to the polyglycerol fatty acid monoester. A mass ratio 2 denotes a ratio of the total mass of the polyglycerol fatty acid monoester and the polyglycerol fatty acid diester to the total mass of the oils or a ratio of the total mass of the polyglycerol fatty acid monoester and the polyglycerol fatty acid triester to the total mass of the oils.

TABLE 1

| | | Example 1 | Example 2 | Example 3 | Example 4 | Example 5 | Example 6 | Example 7 | Example 8 | Example 9 | Example 10 | Example 11 |
|---|---|---|---|---|---|---|---|---|---|---|---|---|
| A | water | QS 100 | QS 100 | QS 100 | QS 100 | QS 100 | QS 100 | QS 100 | QS 100 | QS 100 | QS 100 | QS 100 |
| | dicaprylyl ether | 2 | 3 | — | 2.5 | 2.5 | 10 | 1.5 | 1.5 | 3 | 3 | 3.6 |
| | isohexadecane | 2 | — | 3 | 2.4 | 2.5 | — | 1.5 | 1.5 | — | — | — |
| | squalene | — | — | — | 0.1 | — | — | — | — | — | — | — |
| | polyglyceryl-6 dicaprate | 4 | 3 | 3 | 5 | 4.7 | 5 | 3 | 3 | 3 | 3.3 | 3 |
| | polyglyceryl-6 caprylate | 4 | 3 | 3 | 5 | 4.7 | 5 | 3 | 3 | 5 | 3 | 3 |
| B | sodium cocoyl glycinate | 0.18 | 0.197 | 0.197 | 0.197 | 0.197 | 0.3 | — | — | 0.045 | 0.165 | 1 |
| | disodium cocoyl glutamate | — | — | — | — | — | — | 0.606 | — | — | — | — |
| | sodium cocoyl glutamate | — | — | — | — | — | — | 0.144 | — | — | — | — |
| | sodium cocoyl isethionate | — | — | — | — | — | — | — | 0.6 | — | — | — |
| | coco-betaine | — | — | — | — | 0.18 | 0.9 | — | — | — | — | — |
| C | methylparaben | 0.3 | 0.3 | 0.3 | 0.3 | 0.3 | 0.3 | 0.3 | 0.3 | — | — | — |
| | caprylyl glycol | 0.2 | 0.2 | 0.2 | 0.2 | 0.2 | 0.2 | 0.2 | 0.2 | 0.1 | 0.1 | 0.1 |
| | phenoxyethanol | — | — | — | — | — | — | — | — | 0.3 | 0.3 | 0.3 |
| | average HLB value | 12.4 | 12.4 | 12.4 | 12.4 | 12.4 | 12.4 | 12.4 | 12.4 | 11.7 | 12.3 | 12.4 |
| | mass ratio 1 | 1.0 | 1.0 | 1.0 | 1.0 | 1.0 | 1.0 | 1.0 | 1.0 | 0.6 | 1.1 | 1.0 |
| | mass ratio 2 | 2.0 | 2.0 | 2.0 | 2.0 | 1.88 | 1.0 | 2.0 | 2.0 | 2.67 | 2.1 | 1.67 |

TABLE 2

|   |   | Example 12 | Example 13 | Example 14 | Example 15 | Example 16 | Example 17 | Example 18 | Example 19 |
|---|---|---|---|---|---|---|---|---|---|
| A | water | QS 100 | QS 100 | QS 100 | QS 100 | QS 100 | QS 100 | QS 100 | QS 100 |
|   | dicaprylyl ether | — | 3 | 2 | 1.5 | 0.2 | 2 | — | 2 |
|   | isopropyl myristate | 3.3 | — | — | — | — | — | 3.3 | — |
|   | isohexadecane | — | — | — | — | — | — | — | 2 |
|   | polyglyceryl-6 dicaprate (HLB10.2) | 2.7 | — | 3 | 3 | 3 | 3 | 2.7 | 4 |
|   | polyglyceryl-6 caprylate (HLB 14.6) | 4 | 2.8 | 3 | 3 | 3 | 3 | 4 | 4 |
|   | polyglyceryl-10 trilaurate (HLB10.4) | — | 3.1 | — | — | — | — | — | — |
| B | sodium cocoyl glycinate | 0.06 | 0.1 | 0.197 | 0.197 | 0.197 | 0.197 | 0.06 | 0.197 |
|   | coco-betaine | — | — | — | 2 | 2 | — | — | — |
| C | caprylyl glycol | 0.1 | 0.1 | 0.1 | 0.1 | 0.1 | — | — | — |
|   | phenoxyethanol | 0.3 | 0.3 | 0.3 | 0.3 | 0.3 | 0.3 | 0.3 | 0.3 |
|   | average HLB value | 12.8 | 12.4 | 12.4 | 12.4 | 12.4 | 12.4 | 12.8 | 12.4 |
|   | mass ratio 1 | 0.7 | 1.1 | 1 | 1 | 1 | 1 | 0.7 | 1 |
|   | mass ratio 2 | 2.0 | 2.0 | 3.0 | 4.0 | 30 | 3.0 | 2.0 | 2.0 |

The compositions in the form of microemulsions obtained in Examples 1 to 19 were evaluated for the appearance, the cleansing power against the water-based makeup stains, the cleansing power against the oil-based makeup stains, the stability, the viscosity, and the feeling of freshness as described below. The results of the evaluation are shown in Table 3 and Table 4.

(Appearance: Transparency)

The appearance of the respective prepared compositions were evaluated as shown below by using a spectrophotometer (PC spectrometer UV2101 manufactured by SHIMADZU CORPORATION) with a quartz cell having an optical path length of 1.0 cm to measure the transmittance at 650 nm:

double circle: transmittance of not lower than 80%;
open circle: transmittance of not lower than 50% and lower than 80%;
open triangle: transmittance of not lower than 30% and lower than 50%; and
cross mark: transmittance of lower than 30%.

(Cleansing Power Against Water-Based Makeup Stains)

After mascara (removable with hot water) was applied on the forearm and left for 30 minutes, the applied part of the mascara was wiped off three times with using a cotton wetted with 2.5 g of each prepared composition. The results of visual observation of removal of the mascara were evaluated according to the following evaluation criteria:

double circle: well removed;
open circle: almost removed with a little mascara left;
open triangle: hardly removed; and
cross mark: not removed.

(Cleansing Power Against Oil-Based Makeup Stains)

After mascara (waterproof type) was applied on the forearm and left for 30 minutes, the applied part of the mascara was wiped off six times with using a cotton wetted with 2.5 g of each prepared composition. The results of visual observation of removal of the mascara were evaluated according to the following evaluation criteria:

double circle: well removed;
open circle: almost removed with a little mascara left;
open triangle: hardly removed; and
cross mark: not removed.

(Stability)

A transparent glass vial filled with each of the compositions was kept under the temperature condition of 50° C. for one month. Each vial was checked for the degrees of changes (transparency, smell, pH, and the state of microemulsion) and was evaluated according to the following evaluation criteria:

double circle: no change;
open circle: a slight decrease in transparency (to be kept not lower than 50%) or a slight change in the appearance but disappearing after the temperature was decreased to room temperature;
open triangle: no occurrence of separation but a relatively large decrease in transparency (to be lower than 50%) or no occurrence of separation but a relatively significant change in the appearance and not disappearing even after the temperature was decreased to room temperature; and
cross mark: occurrence of separation.

(Viscosity)

The viscosity was measured at 30° C. by a B-type (Brookfield) viscometer under the condition of a spindle No. 1 and a predetermined rotation speed and was evaluated according to the following evaluation criteria:

double circle: viscosity of 0.1 to 100 mPa·s; and
cross mark: viscosity of higher than 100 mPa·s.

(Feeling of Freshness)

After the evaluation of the cleansing effects described above, seven members of a panel evaluated the feeling of freshness on the dried skin after the wiping off with cotton according to the following evaluation criteria:

double circle; not less than six members out of the seven members approved the feeling of freshness;
open circle: not less than four members but less than six members out of the seven members approved the feeling of freshness; and
cross mark: less than four members out of the seven members approved the feeling of freshness.

TABLE 3

|  | Example 1 | Example 2 | Example 3 | Example 4 | Example 5 | Example 6 | Example 7 | Example 8 | Example 9 | Example 10 | Example 11 |
|---|---|---|---|---|---|---|---|---|---|---|---|
| appearance | ◎ | ◎ | ◎ | ○ | ○ | ○ | ◎ | ◎ | ○ | ◎ | ○ |
| cleansing power (water-based makeup stains) | ◎ | ◎ | ◎ | ◎ | ◎ | ○ | ◎ | ◎ | ○ | ◎ | ◎ |
| cleansing power (oil-based makeup stains) | ◎ | ◎ | ◎ | ◎ | ◎ | ◎ | ◎ | ◎ | ◎ | ◎ | ◎ |
| stability | ◎ | ◎ | ○ | ○ | ○ | ◎ | ◎ | ◎ | ◎ | ○ | ○ |
| viscosity | ◎ | ◎ | ◎ | ◎ | ◎ | ◎ | ◎ | ◎ | ◎ | ◎ | ◎ |
| feeling of freshness | ◎ | ◎ | ◎ | ○ | ○ | ○ | ◎ | ◎ | ◎ | ◎ | ◎ |

TABLE 4

|  | Example 12 | Example 13 | Example 14 | Example 15 | Example 16 | Example 17 | Example 18 | Example 19 |
|---|---|---|---|---|---|---|---|---|
| appearance | ◎ | ○ | ◎ | ○ | ○ | ◎ | ◎ | ◎ |
| cleansing power (water-based makeup stains) | ◎ | ◎ | ◎ | ◎ | ○ | ◎ | ◎ | ◎ |
| cleansing power (oil-based makeup stains) | ◎ | ◎ | ◎ | ○ | ○ | ◎ | ◎ | ◎ |
| stability | ◎ | ◎ | ◎ | ◎ | ◎ | ◎ | ◎ | ◎ |
| viscosity | ◎ | ◎ | ◎ | ◎ | ◎ | ◎ | ◎ | ◎ |
| feeling of freshness | ◎ | ◎ | ◎ | ◎ | ◎ | ◎ | ◎ | ◎ |

Comparative Examples 1 to 10

Cleansing cosmetic compositions of comparative examples were prepared by mixing respective components as shown in Table 5. The HLB value of PEG-6 (glyceryl caprate/caprylate) used in the comparative examples is 13.2. The method of preparation is identical with that of Examples 1 to 19. Numerical values in the tables show "% by mass" of the respective components relative to the total mass of the entire composition.

TABLE 5

|  |  | Comparative Example 1 | Comparative Example 2 | Comparative Example 3 | Comparative Example 4 | Comparative Example 5 |
|---|---|---|---|---|---|---|
| A | water | QS 100 | QS 100 | QS 100 | QS 100 | QS 100 |
|  | dicaprylyl ether | 2 | 2 | 2 | 2 | 2 |
|  | isohexadecane | 2 | 2 | 2 | 2 | 2 |
|  | squalene | — | — | — | — | — |
|  | polyglyceryl-6 dicaprate (HLB 10.2) | 4 | 8 | — | 5 | 4 |
|  | polyglyceryl-6 caprylate (HLB 14.6) | 4 | — | 8 | 3 | 0.8 |
|  | PEG-6 (glyceryl caprate/caprylate) (HLB 13.2) | — | — | — | — | 2.4 |
|  | glycerol | — | — | — | — | — |
|  | (acrylates/alkyl acrylate) crosspolymer | — | — | — | — | — |
| B | sodium cocoyl glycinate | — | 0.18 | 0.18 | 0.18 | 0.18 |
|  | coco-betaine | — | — | — | — | — |
| C | methylparaben | 0.3 | 0.3 | 0.3 | 0.3 | 0.3 |
|  | caprylyl glycol | 0.2 | 0.2 | 0.2 | 0.2 | 0.2 |
|  | phenoxyethanol | — | — | — | — | — |
|  | average HLB value | 12.4 | 10.2 | 14.6 | 11.85 | 10.93 |
|  | mass ratio 1 | 1.0 | — | — | 1.7 | 5.0 |
|  | mass ratio 2 | 2.0 | 2.0 | 2.0 | 2.0 | 1.2 |

|  |  | Comparative Example 6 | Comparative Example 7 | Comparative Example 8 | Comparative Example 9 | Comparative Example 10 |
|---|---|---|---|---|---|---|
| A | water | QS 100 | QS 100 | QS 100 | QS 100 | QS 100 |
|  | dicaprylyl ether | 2 | 0.01 | — | 2 | 3 |
|  | isohexadecane | 2 | — | — | — | — |
|  | squalene | — | — | — | 2 | — |
|  | polyglyceryl-6 dicaprate (HLB 10.2) | 4 | 3 | 3 | 4 | 3 |

TABLE 5-continued

|   |   |   |   |   |   |   |
|---|---|---|---|---|---|---|
|   | polyglyceryl-6 caprylate (HLB 14.6) | — | 3 | 3 | 4 | 3 |
|   | PEG-6 (glyceryl caprate/caprylate) (HLB 13.2) | 4 | — | — | — | — |
|   | glycerol | — | — | — | 8 | — |
|   | (acrylates/alkyl acrylate) crosspolymer | — | — | — | — | 0.2 |
| B | sodium cocoyl glycinate | 0.18 | 0.197 | 0.197 | 0.197 | 0.197 |
|   | coco-betaine | — | 2 | 2 | — | — |
| C | methylparaben | 0.3 | — | — | — | — |
|   | caprylyl glycol | 0.2 | 0.1 | 0.1 | — | — |
|   | phenoxyethanol | — | 0.3 | 0.3 | 0.3 | 0.3 |
|   | average HLB value | 11.7 | 12.4 | 12.4 | 12.4 | 12.4 |
|   | mass ratio 1 | — | 1.0 | 1.0 | 1.0 | 1.0 |
|   | mass ratio 2 | 1.0 | 600 | — | 2.0 | 2.0 |

The compositions obtained in Comparative Examples 1 to 6 were evaluated for the appearance, the cleansing power against the water-based makeup stains, the cleansing power against the oil-based makeup stains, the stability, the viscosity, and the feeling of freshness in the same manner as that of the examples. The results of the evaluation are shown in Table 6. An (acrylates/alkyl acrylate) crosspolymer used in Comparative Example 10 was (acrylates/C10-30 alkyl acrylate) crosspolymer having the viscosity of 10000 to 15000 mPa·s in a 1% aqueous solution adjusted to pH of 6.8.

TABLE 6

|   | Comparative Example 1 | Comparative Example 2 | Comparative Example 3 | Comparative Example 4 | Comparative Example 5 |
|---|---|---|---|---|---|
| appearance | Δ | X | X | X | ⊚ |
| cleansing power (water-based makeup stains) | ⊚ | ○ | X | ⊚ | ⊚ |
| cleansing power (oil-based makeup stains) | Δ | X | X | X | ○ |
| stability | X | X | X | X | X |
| viscosity | ⊚ | ⊚ | ⊚ | ⊚ | ⊚ |
| feeling of freshness | ⊚ | ⊚ | ⊚ | ⊚ | ⊚ |

|   | Comparative Example 6 | Comparative Example 7 | Comparative Example 8 | Comparative Example 9 | Comparative Example 10 |
|---|---|---|---|---|---|
| appearance | Δ | ⊚ | ⊚ | ⊚ | X |
| cleansing power (water-based makeup stains) | ⊚ | Δ | Δ | ⊚ | ⊚ |
| cleansing power (oil-based makeup stains) | ⊚ | X | X | ○ | ⊚ |
| stability | X | ⊚ | ⊚ | ⊚ | ⊚ |
| viscosity | ⊚ | ⊚ | ⊚ | ⊚ | X |
| feeling of freshness | ⊚ | ⊚ | ⊚ | X | X |

As clearly shown in Comparative Examples 9 and 10, substantial inclusion of a polymer such as a polyol or the (acrylates/C10-30 alkyl acrylate) crosspolymer or substantial inclusion of a polyol such as glycerol lowers the feeling of freshness in the state that the composition is not rinsed off with water. Inclusion of the (acrylates/C10-30 alkyl acrylate) crosspolymer increases the viscosity and makes it difficult to be used for wiping with a sheet base material or to be used in a pump foamer.

As clearly understood from the foregoing, the present disclosure provides the cosmetic composition in the form of an oil-in-water (O/W) type emulsion that has the high transparency and the high stability and that also has the high cleansing power against both the water-based makeup stains and the oil-based makeup stations when the cosmetic composition is used as a cleansing cosmetic. The stable microemulsion is formed even when only a small amount of a polyol is included like Examples 1 to 16 or even when no polyol or no (acrylates/C10-30 alkyl acrylate) crosspolymer is included like Examples 17 to 19. This configuration provides the cosmetic composition that has low stickiness and good feeling of freshness even in the state that the cosmetic position is not rinsed off with water. Accordingly, the present disclosure provides the cosmetic composition suitable for cleansing cosmetics of the wiping use-type with a cotton sheet or the like and for leave-on products (skincare products, makeup products and the like intended to be left on the skin, for example, skin lotions, milky lotions, creams, and cosmetic face masks). Furthermore, the cosmetic composition of the present disclosure has a low viscosity and thus allows for wiping use with a cotton sheet or the like or for use in a pump foamer, when being applied as a cleansing cosmetic.

The present disclosure is not limited to the configuration of the embodiment described above but may be modified, altered, changed, replaced, deleted or the like in any of various ways without departing from the subject matter of the present disclosure. Such modifications, alterations, changes, replacements, deletions and the like are included in the scope of the present disclosure. The configuration of the embodiment described above includes either one of the polyglycerol fatty acid diester and the polyglycerol fatty acid triester. A configuration including both the diester and the triester is also included in the scope of the present disclosure. When the cosmetic composition of the present disclosure is applied as a cleansing cosmetic, the method of use is not limited to the wiping use with cotton or the like.

What is claimed is:

1. A cosmetic composition in a form of an oil-in-water type microemulsion, comprising:
    at least one type of an oil;
    at least one type of a polyglycerol fatty acid monoester having an HLB value of 11 to 18;
    at least one type of a polyglycerol fatty acid diester or a polyglycerol fatty acid triester having an HLB value of 10 to 13 and having an alkyl chain or an alkenyl chain of ten to fourteen carbon atoms;
    at least one type of an anionic surfactant; and
    water, wherein;
        a mass ratio of the polyglycerol fatty acid diester or polyglycerol fatty acid triester to the polyglycerol fatty acid monoester is 0.01 to 1.65,
        a ratio of a total mass of the polyglycerol fatty acid monoester and the polyglycerol fatty acid diester or polyglycerol fatty acid triester to a mass of the oil is 1 to 550, and
        the cosmetic composition does not include a polyol, or include a polyol of lower than 1.0% by mass.

2. The cosmetic composition according to claim 1, wherein the cosmetic composition having a viscosity of 0.1 to 100 mPa·s at 30° C.

3. The cosmetic composition according to claim 1, wherein the cosmetic composition does not substantially include (acrylates/C10-30 alkyl acrylate) crosspolymer.

4. The cosmetic composition according to claim 1, wherein the polyglycerol fatty acid monoester has a polyglyceryl moiety derived from two to ten glycerol molecules and an alkyl chain or an alkenyl chain of six to twelve carbon atoms, and the polyglycerol fatty acid diester or polyglycerol fatty acid triester is a polyglycerol fatty acid diester having a polyglyceryl moiety derived from two to ten glycerol molecules.

5. The cosmetic composition according to claim 1, wherein the polyglycerol fatty acid monoester has a polyglyceryl moiety derived from two to ten glycerol molecules and an alkyl chain or an alkenyl chain having six to twelve carbon atoms, and the polyglycerol fatty acid diester or polyglycerol fatty acid triester is a polyglycerol fatty acid triester having a polyglyceryl moiety derived from two to ten glycerol molecules.

6. The cosmetic composition according to claim 1, wherein a mass ratio of the polyglycerol fatty acid diester or polyglycerol fatty acid triester to the polyglycerol fatty acid monoester is 0.6 to 1.1.

7. The cosmetic composition according to claim 1, wherein a mass average HLB value of a mixture of the polyglycerol fatty acid monoester and the polyglycerol fatty acid diester or polyglycerol fatty acid triester is 10.5 to 14.5.

8. The cosmetic composition according to claim 1, wherein a ratio of a total mass of the polyglycerol fatty acid monoester and the polyglycerol fatty acid diester or polyglycerol fatty acid triester to a mass of the oil is 1.66 to 30.

9. The cosmetic composition according to claim 1, wherein the anionic surfactant is at least one type of a surfactant selected from amino acid surfactants and isethionic acid surfactants.

10. The cosmetic composition according to claim 1, wherein the oil is a hydrocarbon oil, an ether oil, or an ester oil.

11. The cosmetic composition according to claim 1, the cosmetic composition being applied to a wiping-type cleansing cosmetic or a leave-on cosmetic.

12. A cosmetic composition in a form of an oil-in-water type microemulsion, comprising:
    at least one type of an oil;
    a polyglyceryl-6 caprylate having an HLB value of 11 to 18;
    a polyglyceryl-6 diacaprate having an HLB value of 10 to 13;
    at least one type of an anionic surfactant; and
    water, wherein:
        a mass ratio of the polyglycerol fatty acid diester or polyglycerol fatty acid triester to the polyglycerol fatty acid monoester is 0.01 to 1.65, and
        a ratio of a total mass of the polyglycerol fatty acid monoester and the polyglycerol fatty acid diester or polyglycerol fatty acid triester to a mass of the oil is 1 to 550.

13. A cosmetic composition in a form of an oil-in-water type microemulsion, comprising:
    at least one type of an oil;
    a polyglyceryl-6 caprylate having an HLB value of 11 to 18;
    a polyglyceryl-10 trilaurate having an HLB value of 10 to 13;
    at least one type of an anionic surfactant; and
    water, wherein:
        a mass ratio of the polyglycerol fatty acid diester or polyglycerol fatty acid triester to the polyglycerol fatty acid monoester is 0.01 to 1.65, and
        a ratio of a total mass of the polyglycerol fatty acid monoester and the polyglycerol fatty acid diester or polyglycerol fatty acid triester to a mass of the oil is 1 to 550.

* * * * *